US008782518B2

(12) United States Patent
Caraher (10) Patent No.: US 8,782,518 B2
(45) Date of Patent: Jul. 15, 2014

(54) MULTILINGUAL FORMS COMPOSER

(76) Inventor: Charles E. Caraher, Brooklyn, NY (US)

(*) Notice: Subject to any disclaimer, the term of this patent is extended or adjusted under 35 U.S.C. 154(b) by 0 days.

(21) Appl. No.: 13/101,501

(22) Filed: May 5, 2011

(65) Prior Publication Data

US 2011/0276871 A1   Nov. 10, 2011

Related U.S. Application Data

(60) Provisional application No. 61/331,467, filed on May 5, 2010.

(51) Int. Cl.
| | |
|---|---|
| *G06F 17/00* | (2006.01) |
| *G06F 17/22* | (2006.01) |
| *G06F 17/24* | (2006.01) |
| *G06F 19/00* | (2011.01) |

(52) U.S. Cl.
CPC .......... *G06F 17/2288* (2013.01); *G06F 17/243* (2013.01); *G06F 19/363* (2013.01)
USPC ........................... 715/265; 715/221; 715/264

(58) Field of Classification Search
USPC .......... 715/200, 221, 224, 226, 255, 264, 265
See application file for complete search history.

(56) References Cited

U.S. PATENT DOCUMENTS

| | | | |
|---|---|---|---|
| 6,434,518 B1 | 8/2002 | Glenn | |
| 6,954,896 B1* | 10/2005 | Dodrill et al. | 715/234 |
| 6,990,441 B1 | 1/2006 | Bolme | |
| 7,949,691 B1* | 5/2011 | Franciscus De Heer et al. | 707/822 |
| 2002/0007287 A1* | 1/2002 | Straube et al. | 705/3 |
| 2004/0098246 A1 | 5/2004 | Welch | |
| 2005/0033567 A1* | 2/2005 | Sukehiro | 704/8 |
| 2007/0163583 A1* | 7/2007 | Brand et al. | 128/203.23 |
| 2009/0035740 A1* | 2/2009 | Reed et al. | 434/265 |
| 2009/0282333 A1* | 11/2009 | Olsen et al. | 715/703 |
| 2011/0313258 A1* | 12/2011 | Chopra et al. | 600/300 |
| 2012/0215360 A1* | 8/2012 | Zerhusen et al. | 700/275 |

\* cited by examiner

*Primary Examiner* — Stephen Hong
*Assistant Examiner* — Gregory J Vaughn
(74) *Attorney, Agent, or Firm* — Adler Vermillion, LLP (57) ABSTRACT

Digital documents are pre-loaded with expressions of underlying data in a plurality of output languages. Expressions of the underlying data are alternatively presented to users to facilitate data collection and information transfer between people who do not share a common language.

13 Claims, 7 Drawing Sheets

MULTILINGUAL FORMS COMPOSER

CROSS REFERENCES TO RELATED APPLICATIONS

This application claims the benefit of Applicant's prior provisional application, application No. 61/331,467 filed on May 5, 2010.

FIELD OF INVENTION

Computer based language translation devices.

BACKGROUND

The following relates to the facilitation of communications between two people who do not share a common language. It may be applied to hospital communications between doctors and patients, and will be described with particular reference thereto. The following may also be applied to any type of inter-language communication, data collection, and a variety of similar applications. For example, "doctor" shall be read to include doctors, nurses, any type of health care provider, and any type of person or system that needs to collect data and/or provide instructions; "hospital" shall be read to include any type of health care institution, and any institution that collects data and keeps records; and "patient" shall be read to include hospital patients, as well as any other type of person or system that is required to provide data and/or receive instructions.

Hospitals typically use hundreds of different forms to gather medical data from their patients, additional forms to provide instructions, and still other forms to collect patient signatures. These forms may cover anything from administration of medicine, to proper diet, to the acknowledgement of informed consent. Hospitals expend significant resources keeping these forms in stock, organized, and readily accessible. Inventory complexity increases significantly when forms are required in multiple languages.

In addition to the inventory and organizational problems, there are inter-language communication problems. If the doctor and patient do not share a common language, the doctor will have trouble explaining the form to the patient, and may be unable to elicit a meaningful response. Patients may describe their conditions more accurately in response to diagnosis forms in their own language. Likewise, printed health care instructions are nearly useless if written in a language the patient cannot understand.

Although a variety of "on the fly" or "real time" software based translation solutions exist, their translations are prone to errors. Translation accuracy is critical for medical diagnosis and patient instruction.

Hospitals often employ human translators. While expert human translators provide accurate translations, they are expensive, and often unavailable (especially at night).

Therefore, there is a need for a system to keep an inventory of documents in a plurality of languages in stock and readily accessible. Furthermore, there is a need for a high-accuracy system to facilitate the explanation and discussion of such forms and documents between people who do not share a common language.

SUMMARY

Applicant's interactive multilingual forms ("Multilingual Forms") solve many of the problems associated with traditional form archives. Multilingual Forms are digital documents capable of alternatively presenting similar data in a plurality of languages. Multilingual Forms may include mechanisms to accept and record user data. Multilingual Directives are a type of Multilingual Form adapted to communicate at least an instruction to another person.

In the medical field, for example, Multilingual Forms may be used to gather patient information, diagnose medical conditions, provide instructions, and record patient input, even if the doctor and patient do not share a common language.

A Multilingual Form may express the same underlying information in a plurality of languages. The original language expression and target language expression(s) are provided in advance, and may be checked for accuracy. This reduces the possibility of translation error.

A Multilingual Form includes a language selection option. The language selection option changes the displayed language. This allows a user to read the form in his preferred language, and then change the displayed language to facilitate communication of the underlying information to another person.

For example, a doctor could read a question to the patient, draw the patient's attention to a picture, phrase, or diagram on the Multilingual Form, and then change the Multilingual Form's display language. Although the language changes, the substantive information represented by the language does not. The patient may now read the same question in his or her own language, and select from a series of answers in his or her own language. The doctor may then revert the screen back to the base language to read the response selected by the patient. Since the output in the patient's language mirrors the output in the doctor's language, the doctor may accurately refer to a particular word, phrase or graphic item in the patient's language, even if the doctor does not understand language currently displayed by the Multilingual Form.

Certain embodiments of a Multilingual Form may include embedded audio or multimedia files. These files may contain a brief prerecorded presentation, in the patient's native language, explaining the content of the Multilingual Form and what information is required from the patient. A different version of the file is recorded in each desired target language. Each version is associated with the Multilingual Form expression of the corresponding target language; that is, the audio or multimedia presentation will be in the same language that is currently being displayed on the Multilingual Form.

An example of a hypothetical use is illustrative. Imagine a doctor who only speaks English, and a patient who only speaks Spanish. The doctor opens the Multilingual Form and selects English as the output language. Line 3 of the English version of this hypothetical form asks "where does it hurt?" After reviewing the information, the doctor may then select the patients preferred language: Spanish. The English expression of the Multilingual Form is replaced by the Spanish expression of the same form. Although the displayed language changes, the substantive information represented by the language remains displayed in the same general locations on the Multilingual Form. The doctor may then point to line three, and confidently interpret any response from the patient as an indication of where the patient is feeling pain. Where responses are not amenable to manual pointing or gesturing, the patient may input data directly onto the tablet. This input data may include, without limitation, selecting answers from a list of choices, writing free responses by hand, or indicating consent to a contract (such as by signature).

In an exemplary embodiment, hard copies of the Multilingual Form may be printed, as amended by the user input. The amended Multilingual Form may also be emailed, saved digitally, or otherwise made part of the patient's electronic medical record.

Although this invention has been discussed in a medical environment, it can be used in any situation requiring accurate translations or the use of forms in a plurality of languages.

DETAILED DESCRIPTION AND PREFERRED EMBODIMENT

The Multilingual Forms Composer ("MFC") may be embodied within any number of different hardware and software combinations. The preferred embodiment is run on a "Motion C5V" tablet PC made by Motion Computing, Inc. Other embodiments may be run on laptops, cell phones, tablet computers, or other computers.

The exemplary embodiment is written in the Microsoft "VB.NET" programming language. This is an exemplary embodiment only; the invention may be written in any programming language.

For the sake of brevity, the following example describes the code of an embodiment with three Multilingual Forms and three Multilingual Directives.

In the exemplary embodiment, the software is driven by data contained in a Microsoft Access database stored on the tablet computer itself. In other embodiments, the database may be stored on a remote server, or in any other readily accessible manner. Other embodiments may utilize other types of databases, including, without limitation, Oracle, Informix or no database at all.

Figure 4:
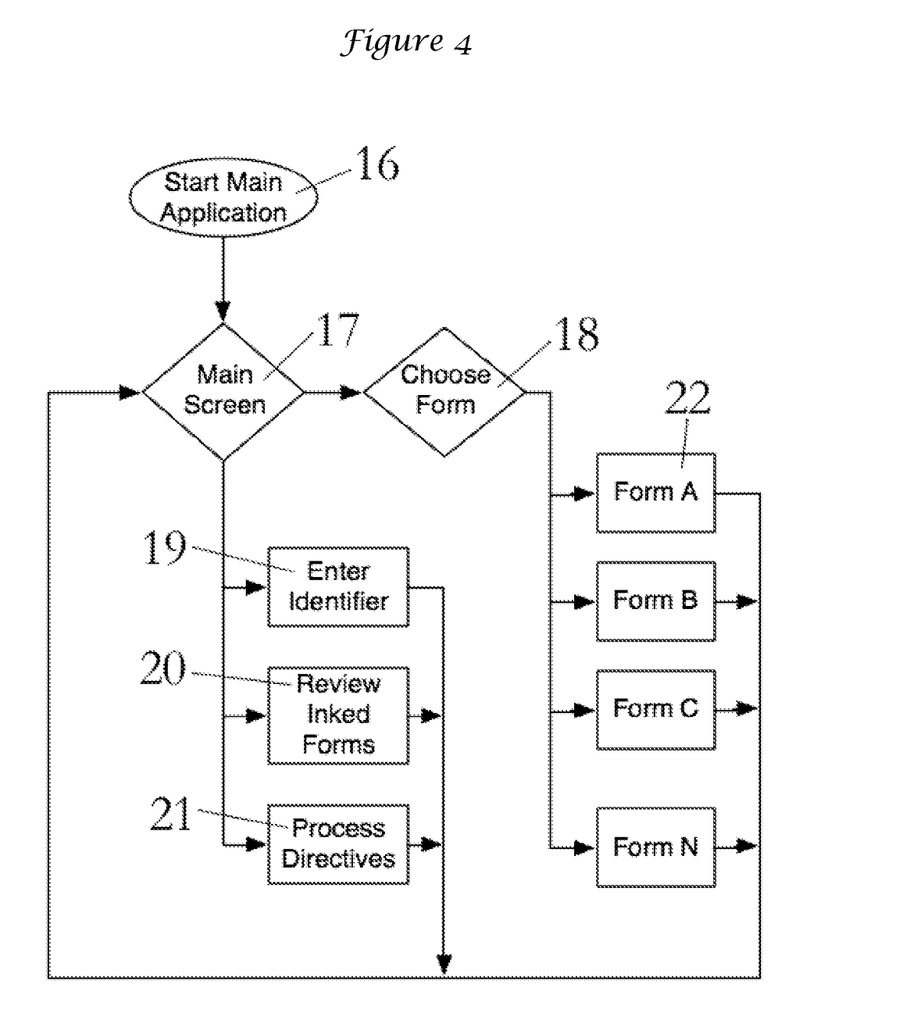
FIG. 4 is a flowchart of the software functions of an exemplary embodiment.
Figure 5:
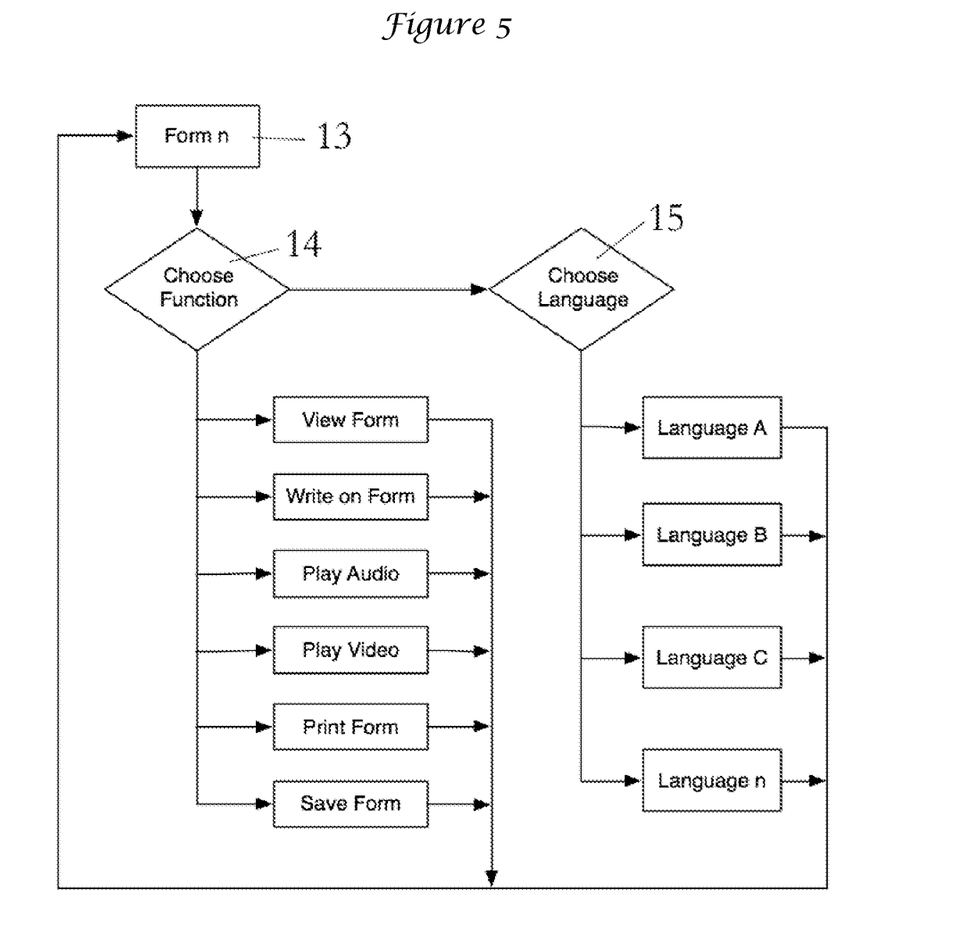
FIG. 5 is a flowchart of the functions of an exemplary Multilingual Form.

In the preferred embodiment, a control table contains the names of the Multilingual Forms and Multilingual Directives to be displayed to the user. Upon initiation 16, the preferred embodiment reads a control table from the database. In this embodiment, the Control Table contains three Multilingual Forms: "Consent, Initial Assessment, and Sublingual Nitroglycerin (note that the "lingual" of "Sublingual Nitroglycerin" refers to a medication placed beneath the tongue, and is unrelated to the inter-language communication features of the "Multilingual Forms Composer"). In the exemplary embodiment, the control table contains three Multilingual Directives: Bleeding Precautions, Interventions, and Pain Assessment. In other embodiments, any number of Multilingual Forms and/or Multilingual Directives may be contained in the control table.

Figure 7:
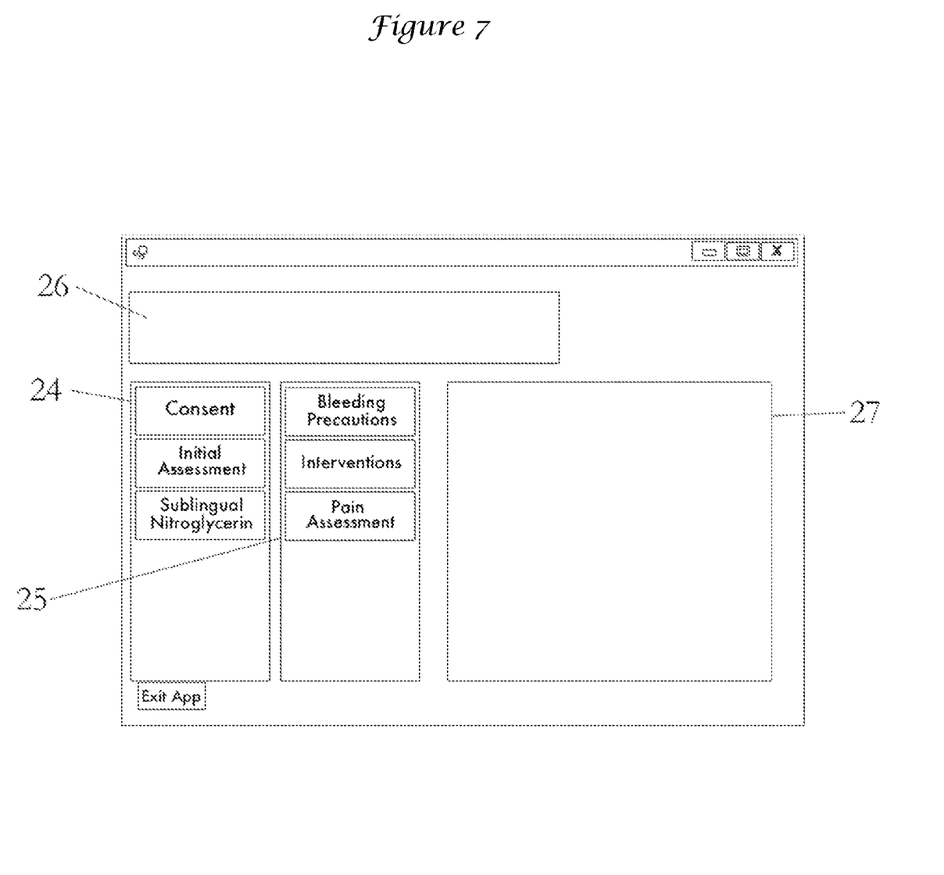
FIG. 7 is an exemplary "Main Screen" from which Multilingual Forms, Multilingual Directives and other programs options may be selected.

The Multilingual Forms and Multilingual Directives may then be displayed to the user in two separate display panels 24, 25 within the "Main Screen" 17—the home screen from which the user controls aspects of the preferred embodiment (FIG. 7 depicts an exemplary "Main Screen").

In the preferred embodiment, forms are loaded into the "Form Panel" 24 within the Main Screen, and directives are loaded into the "Directive Panel" 25 within the Main Screen. The lists of available Multilingual Forms and Multilingual Directives may be displayed to the user as a series of buttons. Pressing a button 14 displays the corresponding Multilingual Form or Multilingual Directive.

Other types of entities may also be presented to the user. For example, a set of video and audio instructions might be presented in a panel. The Main Screen may also present a panel for review of completed forms.

In the preferred embodiment, the Main Screen allows for the input 19 of a patient identifier 26 to enhance organization and archiving of data. The patient identifier may be input as handwritten text. The exemplary embodiment processes the handwritten text, converting it into ASCII text. In other embodiments, the patient identifier may be input by a physical keyboard, an onscreen keyboard or any other data entry method. The patient identifier may be stored and applied to each Multilingual Form used in the interaction.

In the preferred embodiment, pressing a form button on the Main Screen 17 activates the associated Multilingual Form 13. That is, pressing a form button causes the software to access 18 the corresponding table in the database, and display the accessed form 22 information. Likewise, selecting a directive button causes the software to access the corresponding table in the database, and display the accessed Multilingual Directive on the screen.

Figure 1:
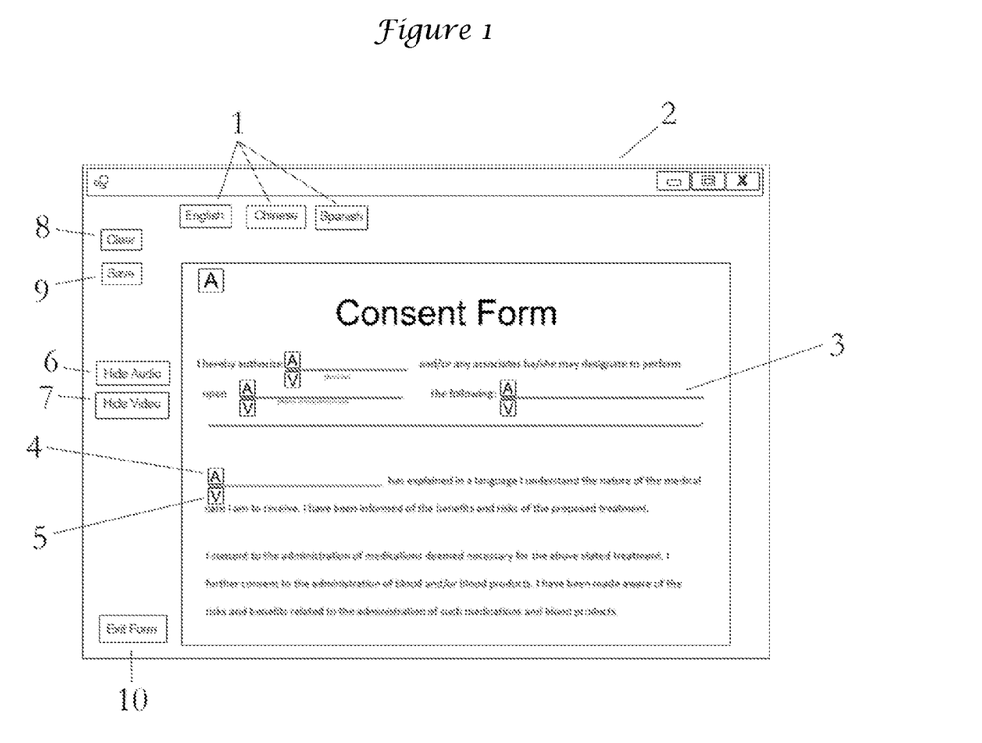
FIG. 1 is an exemplary Multilingual Form as displayed in English.

When selected, the Multilingual Form displays its contents in the default language and presents a variety of function options 14. FIG. 1 depicts an exemplary "Consent" Multilingual Form 2 displayed in English. The Multilingual Form is available to be read by the user, in this example a doctor, in English. A language selection button 1 may then be activated 15 to alternate the displayed output language to the patients preferred language.

The exemplary Multilingual Form contains data entry lines 3 to collect patient data. Data may be entered into these lines and saved 9 in an appropriate database. Erroneous data may be cleared 8 and an option is available to exit the form 10 and return to the Main Screen.

Figure 2:
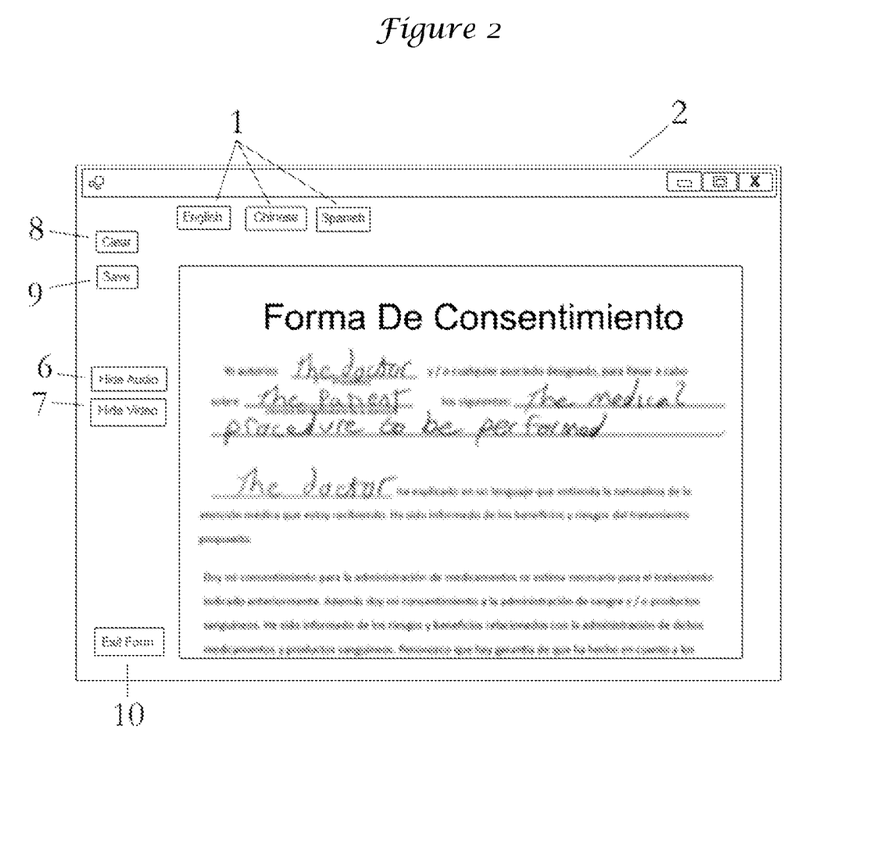
FIG. 2 is an exemplary Multilingual Form as displayed in Spanish.
Figure 3:
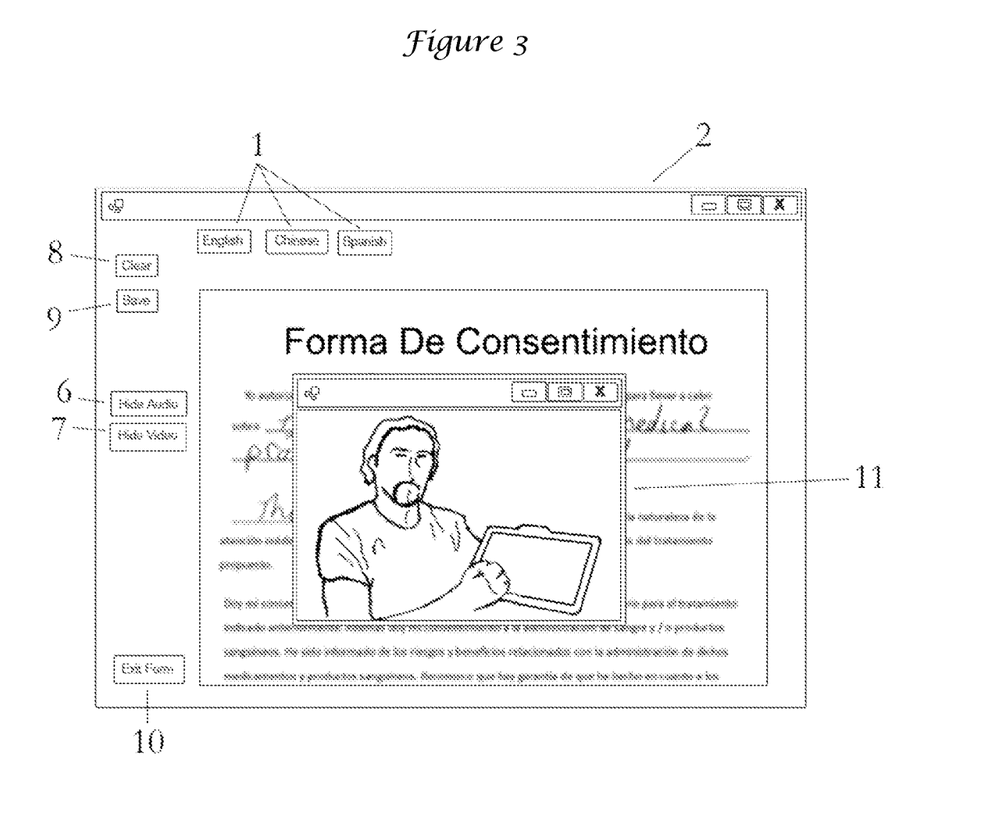
FIG. 3 is an exemplary Multilingual Form as displayed in Spanish, and presenting a multimedia file.

Multilingual Forms may also display context sensitive audio 4 and video 5 buttons. When an audio button is pressed, context sensitive audio is played in the language of the form being displayed. Likewise, when a video button is pressed, a context sensitive video 11 is played in the language of the form being displayed. For example, when the Multilingual Form is displayed in English, the audio or video plays in English. When the Multilingual Form is displayed in Spanish, the audio and video play in Spanish. The Audio and Video buttons may be hidden 6, 7 when not needed.

After Multilingual Forms are processed and signed, the main screen may display the completed Multilingual Forms in a completed form window 27. The completed Multilingual Forms may be displayed with the patient identifier as a prefix to the filename, and may also be displayed with the language in which the form was processed as a suffix to the filename.

Selecting a completed Multilingual Form from the Main Screen will activate a panel for reviewing 20 completed Multilingual Forms. This completed form panel includes options to print a hardcopy of the signed and completed Multilingual Forms.

Figure 6:
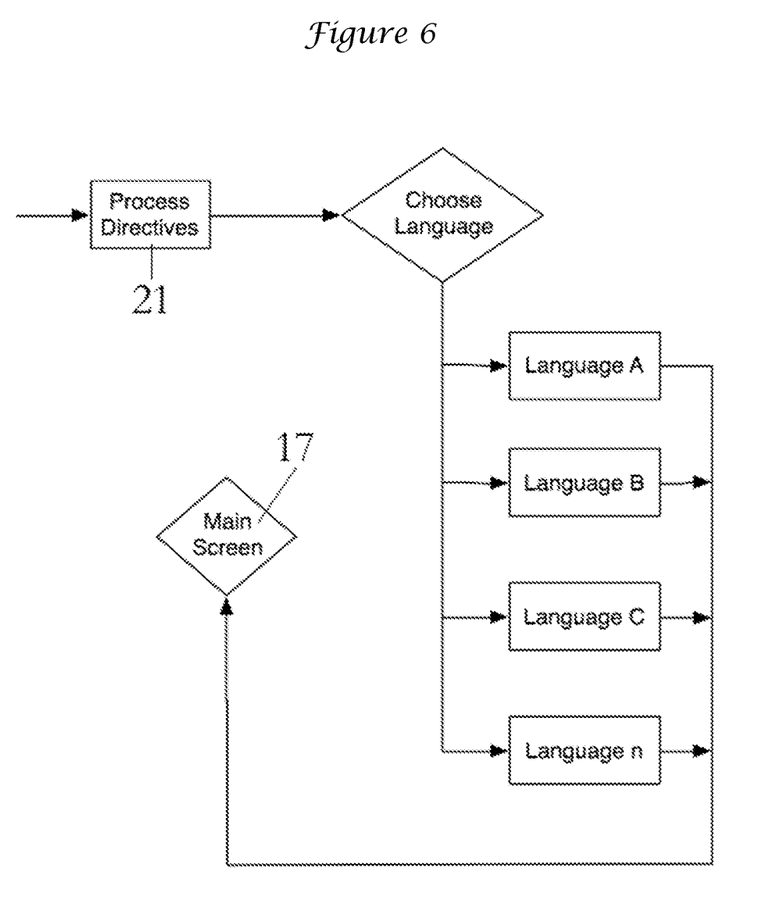
FIG. 6 is a flowchart of the functions of an exemplary Multilingual Directive.

A Multilingual Directive 21 is a variety of Multilingual Form adapted for providing instructions rather than collecting information. Like the Multilingual Form, the Multilingual Directive display includes a plurality of language selection options, such as buttons. Pressing a language selection button changes the display language to the corresponding language.

The selected output language is then used for all output media, including, without limitation, text output, audio output, or video output.

In the exemplary embodiment, the Multilingual Directives contain lists of common commands grouped by patient condition. For example, the "Bleeding Precautions" Multilingual Directive contains commands such as "You must stay in bed until," "You must refrain from eating after," "you can not eat until," "The device around your waist will stay in place until," "you must refrain from bending at the waist until," etc. The Bleeding Precautions Form also contains clock-like circular diagrams divided into twelve hours. The doctor may select an instruction, followed by a time from the clock-diagram (if appropriate). In response, the Multilingual Directive will play an audio file of the directive as spoken in the selected output language. In other embodiments, the audio file may be a multimedia file.

In another embodiment, unfilled paper forms may be printed on the fly, in needed languages. This may reduce inventory demands or even eliminate the need to store hard copies in multiple languages.

In another embodiment, Multilingual Forms accept input from a stylus. Users may write on them like standard paper forms. For example, patients may write an answer out longhand, draw a picture, etc. The Multilingual Forms may record all such input and make it part of the patient's record.

What is claimed is:

1. A computer-implemented medical diagnosis system, comprising:
   a. a memory and a display;
   b. a plurality of multilingual forms stored in the memory
   c. the multilingual forms containing a plurality of diagnostic information in a plurality of predetermined diagnostic-information locations;
   d. two or more language selection buttons,
   e. a plurality of audio activation buttons, each audio activation button located adjacent to a diagnostic-information location,
   f. activation of one of said audio activation buttons causes the system to play an audio clip, wherein
      i. the audio clip explains the diagnostic information adjacent to the activated audio-activation-button, and
      ii. the audio clip explains the diagnostic information in the most recently selected output language.

2. The medical diagnosis system of claim 1, further comprising,
   a. a plurality of video activation buttons, each video activation button located adjacent to a diagnostic information location,
   b. activation of one of said video activation buttons causes the system to play a video clip over the multilingual form, wherein
      i. the video clip explains the diagnostic information adjacent to the activated video-activation-button, and
      ii. the video clip uses the most recently selected output language.

3. The medical diagnosis system of claim 1, further adapted to
   a. accept a patient identifier, and
   b. apply said patient identifier to a saved copy of the Multilingual Forms.

4. The medical diagnosis system of claim 1, further adapted to accept input from a stylus anywhere on the multilingual forms.

5. The medical diagnosis system of claim 1, further comprising a plurality of multi-lingual directives, wherein,
   a. the multilingual directives contains commands grouped by patient condition.

6. The medical diagnosis system of claim 5, further comprising,
   a. a clock-like circular diagram divided into 12 hours, and wherein,
   b. the medical diagnosis system receives a selection of a multilingual directive and the selection of a time.

7. The medical diagnosis system of claim 5,
   a. further adapted to receive a consent input,
   b. said consent input indicating that a user has understood the multilingual directive.

8. The medical diagnosis system of claim 7, wherein
   a. a multilingual directive is associated with a filename, and
   b. wherein the medical diagnosis system further comprises a display screen configured to display a list of a plurality of multilingual filenames.

9. The medical diagnosis system of claim 8, wherein a patient identifier is attached to the filename as a prefix.

10. The medical diagnosis system of claim 8, wherein the language in which the form was processed is attached to the filename as a suffix.

11. The medical diagnosis system of claim 1, wherein the memory stores the multilingual forms in a local database.

12. The medical diagnosis system of claim 1, wherein the memory stores the multilingual forms in a remote server.

13. A computer-implemented medical diagnosis system, consisting of:
   a. a memory and a display;
   b. a plurality of multilingual forms stored in the memory,
      i. the multilingual forms containing a plurality of diagnostic information in a plurality of predetermined diagnostic-information locations;
   c. two or more language selection buttons,
   d. a plurality of audio activation buttons, each audio activation button located adjacent to a diagnostic-information location,
   e. activation of one of said audio activation buttons causes the system to play an audio clip, wherein
      i. the audio clip explains the diagnostic information adjacent to the activated audio-activation-button, and
      ii. the audio clip explains the diagnostic information in the most recently selected output language.

* * * * *